United States Patent [19]

Nakamura et al.

[11] 4,392,933

[45] Jul. 12, 1983

[54] ELECTROCHEMICAL MEASURING APPARATUS COMPRISING ENZYME ELECTRODE

[75] Inventors: Kenichi Nakamura, Hirakata; Shiro Nankai, Neyagawa; Takashi Iijima, Hirakata, all of Japan

[73] Assignee: Matsushita Electric Industrial Co., Ltd., Osaka, Japan

[21] Appl. No.: 358,609

[22] Filed: Mar. 15, 1982

Related U.S. Application Data

[63] Continuation of Ser. No. 90,068, Oct. 31, 1979, abandoned.

[30] Foreign Application Priority Data

Oct. 31, 1978 [JP] Japan .............................. 53-134784

[51] Int. Cl.³ .................... C12Q 1/00; C12Q 1/26
[52] U.S. Cl. .................... 204/403; 204/1 T;
435/176; 435/288; 435/291; 435/817
[58] Field of Search .............. 204/1 E, 195 B, 195 R;
435/176, 288, 291, 817

[56] References Cited

U.S. PATENT DOCUMENTS

| | | | |
|---|---|---|---|
| 3,403,081 | 9/1968 | Rohrback et al. | 204/195 B X |
| 3,539,455 | 11/1970 | Clark | 204/1 T |
| 3,783,101 | 1/1974 | Tomb et al. | 435/176 |
| 3,839,175 | 10/1974 | Keyes | 204/181 |
| 3,912,593 | 10/1975 | Barker et al. | 435/176 |
| 3,926,764 | 12/1975 | Ruzicka et al. | 204/195 F |
| 3,948,745 | 4/1976 | Guilbault et al. | 204/195 B |
| 4,016,044 | 4/1977 | Fresnel et al. | 435/288 X |
| 4,048,018 | 9/1977 | Coughlin et al. | 435/176 X |
| 4,115,198 | 9/1978 | Coughlin et al. | 435/176 |
| 4,152,210 | 5/1979 | Robinson et al. | 435/176 X |
| 4,224,125 | 9/1980 | Nakamura et al. | 204/195 B |

Primary Examiner—G. L. Kaplan
Attorney, Agent, or Firm—Wenderoth, Lind & Ponack

[57] ABSTRACT

An immobilized enzyme electrode effective in measurement of the substrate concentration of the enzyme and in conversion from enzyme reaction energies into electric energies. The immobilized enzyme, of an oxidase system, such as glucose oxidase, amino acid oxidase, xanthine oxidase or the like and a metal oxide capable of constituting a redox system which is reduced through coupling with these enzyme reactions and is electrochemically oxidized (anodic oxidation) are combined with each other. The use of the enzyme electrode allows the determination quantity of the enzyme substrate as extremely low as approximately $10^{-5}$ to $10^{-6}$ mole/l in concentration.

1 Claim, 8 Drawing Figures

ELECTROCHEMICAL MEASURING APPARATUS COMPRISING ENZYME ELECTRODE

CROSS-REFERENCE TO RELATED APPLICATION

This is a continuation of application Ser. No. 90,068, filed Oct. 31, 1979 and now abandoned.

BACKGROUND OF THE INVENTION

The present invention relates to a novel immobilized enzyme electrode which is effective in the measurement of the substrate concentration of enzyme and in the conversion of enzyme reaction energy into electrical energy. More particularly, the present invention relates to an immobilized enzyme electrode wherein an immobilized oxidase, such as glucose oxidase, amino-acid oxidase, xanthine oxidase or the like and a metal oxide, which is reduced through the enzyme reactions and is electrochemically oxidized (anodically oxidized) are combined with each other.

Conventionally, as an enzyme electrode using various immobilized enzymes of an oxidase, there is known an electrode which electrochemically measures the concentration of $O_2$ to be consumed or the concentration of $H_2O_2$ to be produced, in the oxidation reaction of a substrate $AH_2$ to A by an oxidase as shown in FIG. 1, thereby to indirectly measure the substrate concentration.

For example, the specification of the U.S. Pat. No. 3,539,455 describes an enzyme electrode of a $H_2O_2$ detecting system. In this example, $H_2O_2$ is anodically oxidized directly on an electron-collector such as graphite or the like and the oxidation current of the $H_2O_2$ is measured directly. Accordingly, the response time thereof is prolonged due to the diffusion delay of $H_2O_2$. Also, the current tends to be affected by the dissolved oxygen concentration. At the same time, the current value to be obtained is small, with consequent limitation of the oxygen solubility.

SUMMARY OF THE INVENTION

According to the present invention, there is provided a solid state enzyme electrode comprising an oxidase, an electron-collector and a metal oxide provided in electric contact with said electron collector, said oxidase being immobilized onto said metal oxide, said metal oxide being reduced through said oxidase reaction, and being oxidized electrochemically by said electron collector to constitute a redox system, as shown in the reaction principle of FIG. 2.

The metal oxide $MO_x$ couples with the enzyme reaction to produce oxygen and is reduced to $MO_{x-1}$. At the same time, the $MO_{x-1}$ is oxidized to $MO_x$ through electrochemical oxidation, and the anodic oxidation current is obtained in a process where the $MO_{x-1}$ is converted to $MO_x$. Accordingly, the metal oxide is required to be previously kept in contact with the electron collector. An oxide such as manganese, ruthenium, vanadium, cobalt, nickel, silver, lead, platinum, iridium, osmium, niobium or the like was found to be effective as a metal oxide capable of constituting the redox system reduced through coupling with the enzyme reaction and electrochemically oxidized by the electron collector.

Since the present invention is different from a method of measuring $O_2$ or $H_2O_2$ which is a reactant or a product in the conventional example, the present invention is extremely improved in sensitivity and response properties as sufficiently expected in principle. In addition thereto, the present invention is advantageous in terms of the life, drift, and the stability, etc. of the metal oxide itself as compared with a method of using a redox polymer or the like as already proposed by the inventors.

Therefore, a principal object of the present invention is to provide a novel immobilized enzyme electrode which is effective in the measurement of the substrate concentration of the enzyme and in the conversion of the enzyme reaction energy into electrical energy.

Another object of the present invention is to provide a novel immobilized enzyme electrode having the novel features as set forth above.

These objects and other objects, features, aspects and advantages of the present invention will become more apparent from the following detailed description when taken in conjunction with the accompanying drawings.

DESCRIPTION OF THE PREFERRED EMBODIMENTS

The following Examples 1 to 4 will describe in detail the construction of the enzyme electrode of the present invention and the measurement of the substrate concentration using the enzyme electrode.

EXAMPLE 1

In the preparation of the basic materials, glucose oxidase is used as an oxidase, ruthenium oxide $RuO_2$ as a metal oxide, and graphite as an electron collector.

First, $RuO_2$ powder and graphite powder is mixed with each other, and the mixed powder is molded by a press into a disc type. Then, after a glucose oxidase solution has been applied upon one surface of the molded disc and dried, glutaraldehyde acts to immobilize the glucose oxidase. In this manner, the glucose oxidase is immobilized onto the $RuO_2$, and the $RuO_2$ is in contact with the graphite.

Figure 1:
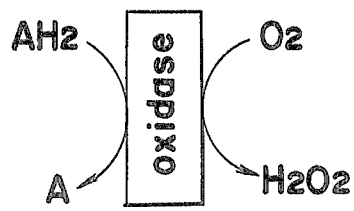
FIG. 1 is a schematic view showing a normal reaction of an oxidase.
Figure 2:
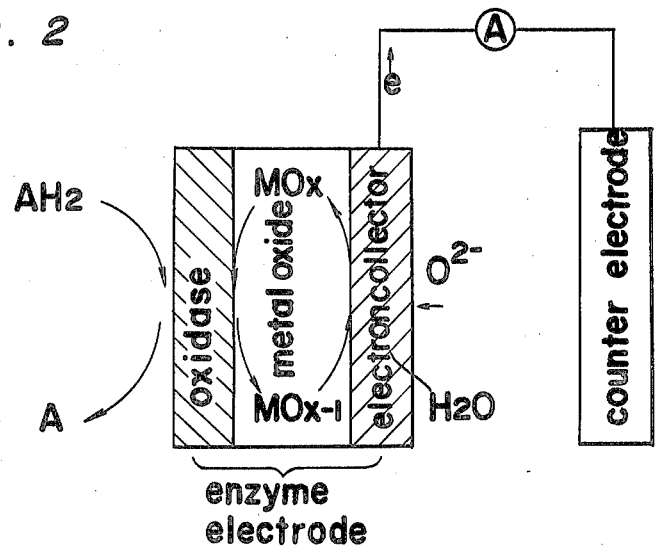
FIG. 2 is a schematic view showing the enzyme electrode of the present invention connected to a counter electrode.
Figure 3:
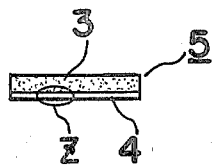
FIG. 3 is a longitudinal cross-sectional view of an enzyme electrode in one embodiment of the present invention.
Figure 4:
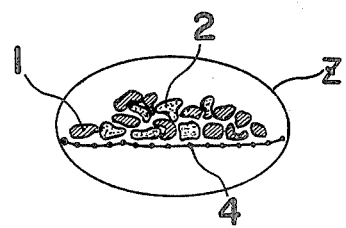
FIG. 4 is a schematic view showing, on an enlarged scale, the portion Z of FIG. 3.

FIG. 3 and FIG. 4 show schematically the enzyme electrode of the present invention, wherein the powder of the metal oxide $RuO_2$ is designated at 1 and 4, the powder of the electron collector graphite is designated at 2. The molded disc 3 of the $RuO_2$ 1 and the graphite mixture is formed as one solid unit, and the enzyme glucose oxidase 4 is immobilized through cross-linking on the surface of the disc 3. Thus the $RuO_2$, the graphite, and the immobilized glucose oxidase as a whole constitute a solid state enzyme electrode.

Figure 5:
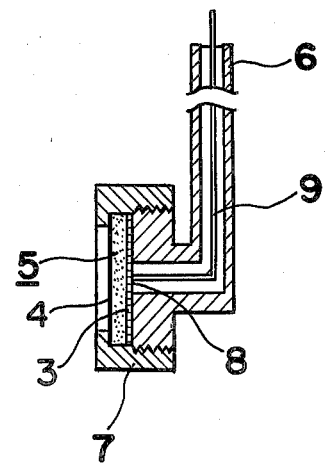
FIG. 5 is a longitudinal cross-sectional view of an electrode holder employed within the present invention.

FIG. 5 shows an electrode holder with the above enzyme electrode 5 built-in. A cylindrical holder 6 is made of an insulator, and a screw 7 is adapted to fix the electrode 5 to the holder 6. Glucose oxidase 4 is immobilized on one surface of the disc 3, and the other surface thereof is in electrical contact with the platinum plate 8. A lead wire 9 is connected to the platinum plate 8.

Figure 6:
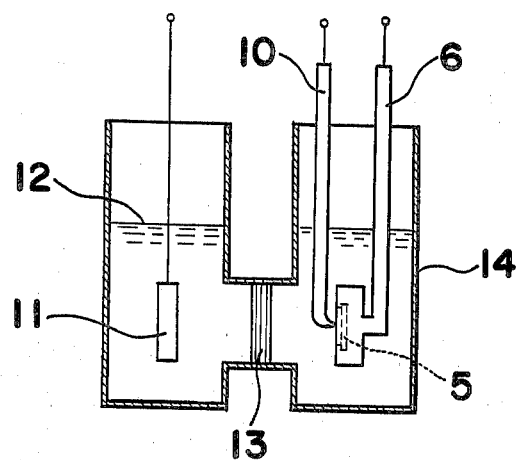
FIG. 6 is a longitudinal cross-sectional view showing an enzyme electrode built-in to an electrochemical measurement system.

FIG. 6 shows an electrochemical measurement system with the electrode holder 6 built-in, and the electrode holder 6 being provided with the abovedescribed enzyme electrode 5. A reference electrode 10, provided near the electrode 5 is composed of a saturated calomel electrode SCE. A counter electrode 11 is provided in front of the electrode 5. A phosphate buffer 12 is placed in a cell 14 provided with a separator 13. The electrode 5 and reference, electrode 10 are immersed within the phosphate buffer at one side of the separator 13, while the counter electrode 11 is placed within the phosphate buffer at the other side.

In this measurement system, glucose is injected into the phosphate buffer on the enzyme electrode side, with the enzyme electrode being set in constant potential to 0.3 V with respect to the reference electrode 10, to measure the variation in anodic current flowing between the enzyme electrode 5 and the counter electrode 11.

Figure 7:
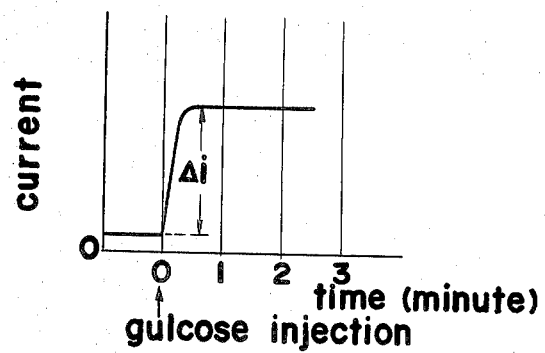
FIG. 7 is a current response curve for the enzyme electrode; of the present invention by a glucose injection as an embodiment of the present invention.
Figure 8:
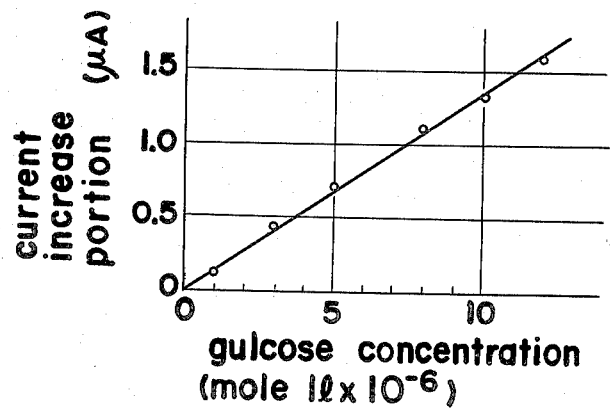
FIG. 8 illustrates the relationship between the glucose concentration and the current increase portion.

FIG. 7 shows a current response curve obtained in this Example 1. The current increases rapidly through injection of glucose to reach a steady-state value in approximately 0.5 minute. FIG. 8 shows the relationship between the concentration of the injected glucose and the current increase portion $\Delta i$ of FIG. 7. It is found out from FIG. 8 that the glucose concentration can be measured as far as approximately glucose concentration $10^{-6}$ mole/l.

EXAMPLE 2

The concentration of L-leucine could be measured when present in amounts as low as $10^{-5}$ mole/l by a similar method as the Example 1 where an electrode, which was made in the same manner as the Example 1 except that glucose oxidase was replaced by L-amino acid oxidase, was also built into the same system as that of the Example 1.

EXAMPLE 3

An electrode made in the same manner as that of Example 1 except that xanthine oxidase was used as the oxidase and manganese dioxide $MnO_2$ was used as the metal oxide was also built into the same system as that of Example 1. The electrode was used in measuring the concentration of hypoxanthine under the same conditions as those of the Example 1 except that the setting voltage of the enzyme electrode was changed to 0.4 V with respect to the reference electrode. In this case, the measurement could be made for a hypoxanthine concentration as low as $10^{-6}$ mole/l.

EXAMPLE 4

An electrode made in the same manner as in Example 1 except that D-amino acid oxidase was used as the oxidase and cobalt oxide $Co_2O_3$ was used as the metal oxide was also built into the same system as that of the Example 1. The electrode was used in measuring the concentration of D-alanine under the same conditions as those of the example 1 except that the setting voltage of the enzyme electrode was changed to 0.4 V with respect to the reference electrode. In this case, the concentration of D-alanine could be measured for amounts as low as $10^{-5}$ mole/l.

With respect to the Examples 1 to 4, the details are unknown about the reaction mechanism of the metal oxide $MO_x$ which couples with the enzyme reaction. For example, the redox system of manganese dioxide is different from the redox system of $MO_x \rightleftarrows MO_{x-1}$, but rather the reaction mechanism is considered to be represented by the reaction. $MnO_2 \rightleftarrows MnOOH$. However, in either case the setting potential is required to be set near the potential of higher class oxide $MnO_2$ is stable.

In the Examples 1 to 4, the metal oxide in a powder state is mixed with graphite powder to be molded by a press, the metal oxide can be used to form a thin film through thermal decomposition, electrodeposition, vapor deposition or the like on the electron-collector plate. For example, the thermal decomposition of $RuCl_3$ can be used in the case of $RuO_2$, the thermal decomposition of $Mn(NO_3)_2$ or the electro-decomposition in $MnSO_4$ solution can be used in the case of $MnO_2$ and vapor deposition can be used in the case of $Co_2O_3$. In the Examples 1 to 4 one portion of oxidase is immobilized on the electron collector. In this case, all the enzyme can be immobilized directly on the metal oxide, since the enzyme reaction is further promoted.

Also, a conductive metal oxide such as $RuO_2$, $MnO_2$ can be made by itself to serve as the electron collector. In such a case, the electron collector graphite is not required as in the Examples, and a thin film of metal oxide is formed, through the thermal decomposition of $RuCl_3$ or $Mn(NO_3)_2$ directly on a proper base plate, such as glass plate, With a lead taken directly from the thin film of metal oxide.

As the oxidase, there can be used urate oxidase (uricase), aldehyde oxidase, pyruvate oxidase, oxalate oxidase, lactate oxidase, malate oxidase, cholesterol oxidase, galactose oxidase, thiol oxidase and alcohol oxidase.

Also, the enzyme electrode of the present invention can be used not only in the measurement of the enzyme substrate concentration, but also in the synthesis of oxidation products of various oxidase substrates. In this case, the potential of the enzyme electrode is regulated to control the reaction rate of the synthesis.

As apparent from the above-described examples, the use of the enzyme electrode of the present invention allows the determination quantity of the enzyme substrate to be extremely low as approximately $10^{-5}$ to $10^{-6}$ mole/l. In other words, the oxidase is immobilized extremely close to the metal oxide and the oxygen necessary for enzyme reaction is quickly supplied from the metal oxide and simultaneously the reduced metal oxide is electrochemically formed into the higher oxidation state. As a result, the enzyme reaction is remarkably promoted, thus allowing the measurable current to be obtained even when the substrate concentration is extremely low.

Although the present invention has been described and illustrated in detail, it is to be clearly understood that this is by way of limitation, and the spirit and scope of the present invention is limited only by the terms of the appended claims.

What is claimed is:

1. An electrochemical measuring system for measuring the concentration of a substrate in solution comprising a counter electrode connected to a reference electrode and a solid state enzyme electrode, said solid state enzyme electrode comprising an electron collector, a metal oxide in intimate contact with the electron collector and an oxidase immobilized onto said metal oxide, said electron collector connected to means which make it an anode, wherein said metal oxide is capable of being reduced through an oxidase reaction and oxidized electrochemically through contact with the electron collector; said system further comprising a means for applying a constant potential between said enzyme electrode and said reference electrode and comprising a means for measuring the variation of current flowing between the enzyme electrode and the counter electrode when the system is used to measure the concentration of a substrate as a result of said electrochemical reaction, said measured current corresponding to said concentration of enzyme to be measured.

* * * * *